United States Patent [19]

Yamaguchi

[11] 4,407,272

[45] Oct. 4, 1983

[54] ENDOSCOPE SYSTEM WITH MEANS FOR DETECTING AUXILIARY APPARATUSES

[75] Inventor: Tatuya Yamaguchi, Hino, Japan

[73] Assignee: Olympus Optical Co., Ltd., Tokyo, Japan

[21] Appl. No.: 307,306

[22] Filed: Sep. 30, 1981

[30] Foreign Application Priority Data

Oct. 8, 1980 [JP] Japan ................................ 55/140992

[51] Int. Cl.³ ............................................... A61B 1/06
[52] U.S. Cl. ........................................................ 128/6
[58] Field of Search .................................... 128/4, 5, 6

[56] References Cited

U.S. PATENT DOCUMENTS

| | | | |
|---|---|---|---|
| 3,556,085 | 1/1971 | Takahashi | 128/6 |
| 3,643,653 | 2/1972 | Takahashi et al. | 128/6 |
| 3,994,557 | 11/1976 | Hopkins | 350/33 |
| 4,082,946 | 4/1978 | Heine et al. | 128/6 |
| 4,281,910 | 8/1981 | Takayama | 128/4 |
| 4,325,618 | 4/1982 | Hosoda | 128/6 |

Primary Examiner—Kyle L. Howell
Assistant Examiner—Max F. Hindenburg
Attorney, Agent, or Firm—Frishauf, Holtz, Goodman and Woodward

[57] ABSTRACT

An endoscope system comprises an endoscope, a light source unit, and an auxiliary apparatus such as a camera unit or a dual viewing optical unit. The light source unit includes a discriminating circuit which discriminates the kind of the auxiliary apparatus when the auxiliary apparatus is attached to a viewing section of the endoscope. The discriminating circuit causes a solenoid energizing circuit to drive a solenoid in accordance with the kind of the auxiliary apparatus, thereby moving a stop to a predetermined position. In consequence, illumination light of a given intensity corresponding to the kind of attached auxiliary apparatus is led from a light source into a light guide of the endoscope. Thus, an image can always be observed with suitable brightness through the auxiliary apparatus or the viewing section of the endoscope without regard to the attachment of the auxiliary apparatus, as well as to the kind thereof.

11 Claims, 7 Drawing Figures

ENDOSCOPE SYSTEM WITH MEANS FOR DETECTING AUXILIARY APPARATUSES

BACKGROUND OF THE INVENTION

This invention relates to an endoscope system provided with a luminance adjusting apparatus.

In some endoscope systems, an associated or auxiliary apparatus such as a dual viewing optical unit or camera unit is attached to an eyepiece section so that two or more operators may simultaneously observe the interior of a body cavity, or that the region of interest in the body cavity may be photographed.

In an endoscope system in which a light transmitted from a light source unit through a light guide is projected on the region of interest and a light reflected from the region of interest is transmitted to an eyepiece section through an image guide so that an image of the region may be viewed, when a dual viewing optical unit, a camera with a photometric beam splitter, or a TV camera with a beam splitter capable of simultaneous observation and photographing is attached to the eyepiece section, the light beams supplied to main and auxiliary observation light paths is reduced by the beam splitter, failing to provide a sufficient observation light. When the associated or auxiliary apparatus is removed from the eyepiece section, on the other hand, the beam supplied to the main observation light path will be too large to keep a proper degree of brightness.

Conventionally, therefore, luminance is adjusted by a mechanical stop disposed between a light source lamp and the incidence end face of the light guide, or an electric power control circuit for controlling electric power supplied to the light source lamp.

With the prior art systems, however, the operator must manually regulate luminance with every attachment or detachment of the auxiliary apparatus. Thus, the operation is complicated and troublesome, and the observation time will be prolonged to cause increased pain to a patient.

SUMMARY OF THE INVENTION

An object of this invention is to provide an endoscope system capable of automatic adjustment of luminance.

Another object of the invention is to provide an endoscope system capable of providing an image with suitable brightness through an endoscope or the endoscope and an associated apparatus whether the associated apparatus is or is not attached to the endoscope.

According to the invention, there is provided an endoscope system which comprises an endoscope including a light guide for transmitting an illumination light, an image guide for transmitting a light reflected by a region of interest on which the illumination light from the light guide is projected, and a section for viewing an image of the region of interest transmitted through the image guide, a light source for supplying the illumination light to the light guide of the endoscope, an auxiliary apparatus capable of being attached to and detached from the viewing section of the endoscope, and means for detecting the attachment of the auxiliary apparatus to the viewing section of the endoscope and increasing the luminance of light led into the light guide of the endoscope as a function of the kind of the kind of the attached auxiliary apparatus.

DETAILED DESCRIPTION OF THE PREFERRED EMBODIMENTS

Figure 1:
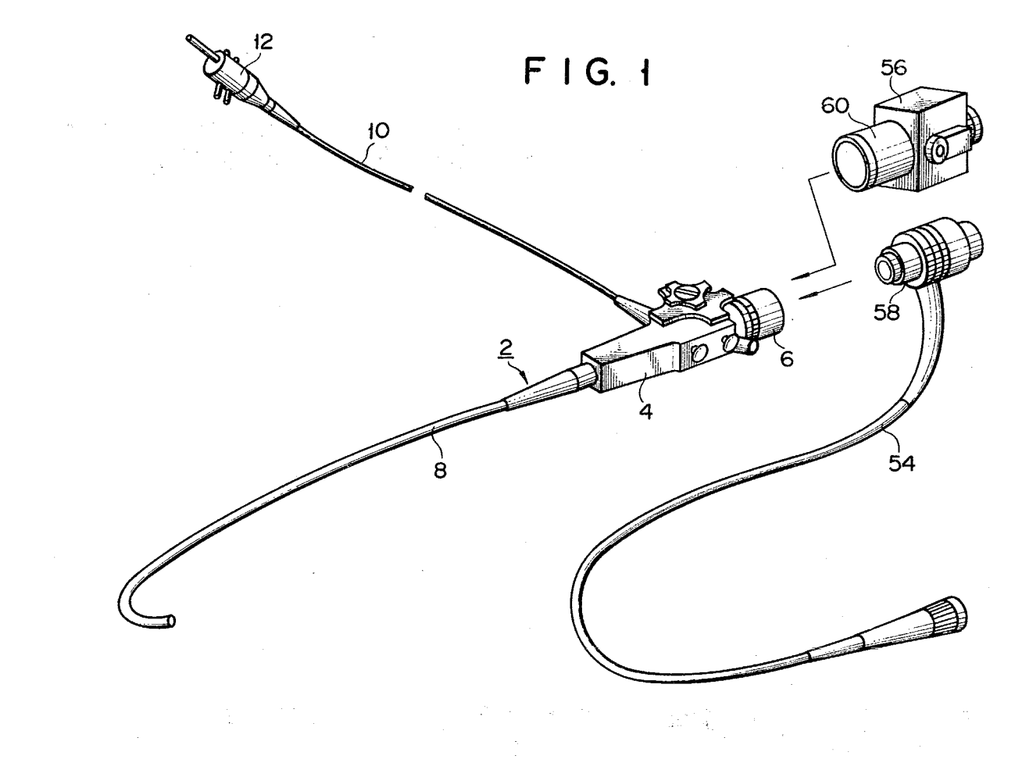
FIG. 1 is a perspective view showing an embodiment of the endoscope system of this invention.
Figure 2:
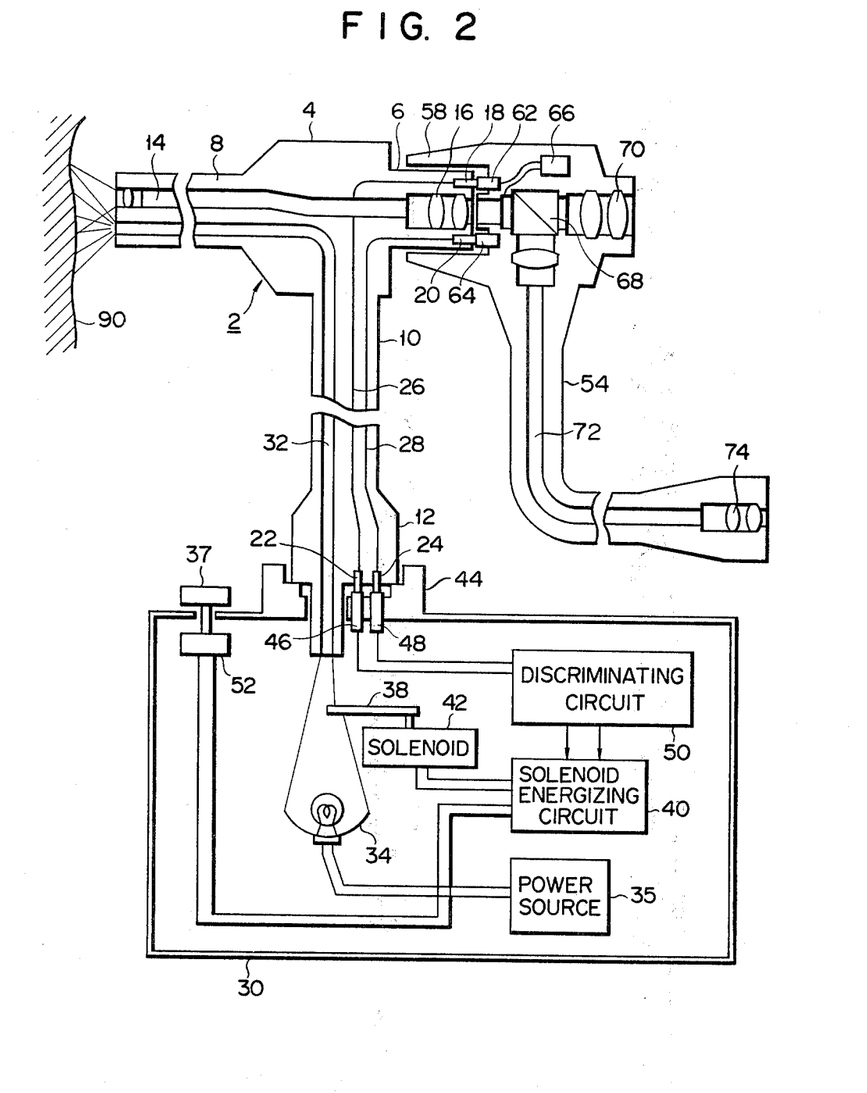
FIG. 2 is a schematic view for illustrating the endoscope system shown in FIG. 1.

Referring now to FIGS. 1 and 2, there is shown an endoscope system according to an embodiment of this invention. As is generally known, a control section 4 of an endoscope 2 is provided with an eyepiece section 6, and is coupled with an insertion section 8. Further, a connector 12 is provided at a one end of a universal cord 10, the other end of which is coupled to the control section 4. An image guide 14 extends in the insertion section 8, the control section 4, and the eyepiece section 6, and an eyepiece lens 16 is disposed on the optical axis of the image guide 14 in the eyepiece section 6. Contacts 18 and 20 exposed to the outside are arranged on the end face of the eyepiece section 6, while connecting pins 22 and 24 exposed to the outside are arranged on the end face of the connector 12. The contacts 18 and 20 and the connecting pins 22 and 24 are connected by means of lead wires 26 and 28, respectively.

In a light source unit 30 connected with the connector 12, a lamp 34 is disposed as a light source for supplying illumination or observation light to the incidence end face of a light guide 32 which extends in the universal cord 10. The lamp 34 is connectd to a power source 35, and a stop 38 is disposed in the illumination light path between the lamp 34 and the light guide 32. The stop 38 is coupled to a solenoid 42 for shifting the stop 38. The light source unit 30 is provided with a connecting portion 44, to which the connector 12 is removably coupled. Connecting pins 46 and 48 are fixed in the connecting portion, which are contacted with the connecting pins 22 and 24 respectively when the connector 12 is attached to the connecting portion 44. The connecting pins 46 and 48 are connected by the lead wires 26 and 28 with a discriminating circuit 50 which detects whether or not an auxiliary apparatus is mounted on the eyepiece section 6 of the endoscope 2 and discerns the kind of the auxiliary apparatus. The discriminating circuit 50 is connected with a solenoid energizing circuit 40 for energizing the solenoid 42 in accordance with signals supplied from the discriminating circuit 50. The solenoid energizing circuit 40 is connected to a variable resistor or a rotary switch 52 which is coupled to a luminance adjusting knob 37 attached to the light source unit 30.

Figure 3:
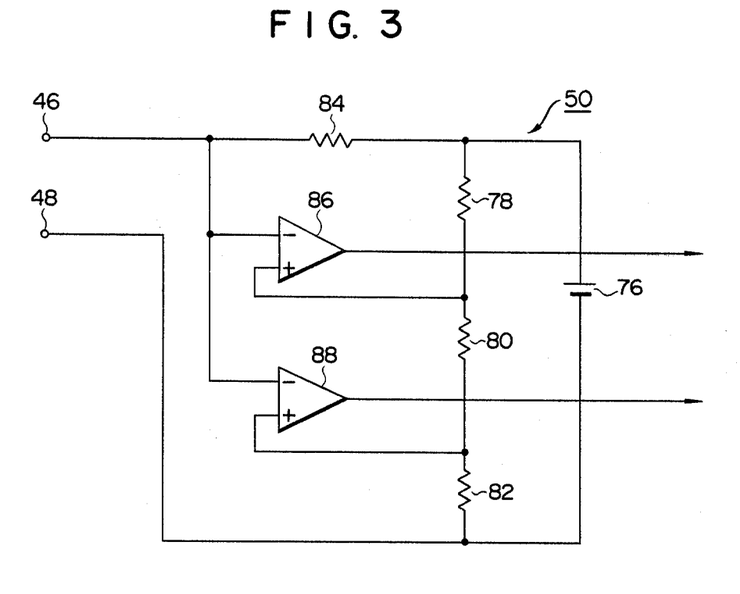
FIG. 3 is a circuit diagram showing an example of a discriminating circuit shown in FIG. 2.

Disposed in respective mounting sections 58 and 60 of a dual viewing optical unit 54 and a camera unit 56 as auxiliary apparatuses to be attached to the eyepiece section 6 of the endoscope 2 are connecting pins 62 and 64 which are to be connected with the connecting pins 18 and 20 in the eyepiece section 6. These connecting pins 62 and 64 are connected also with a code generator 66 such as a resistor for indicating the kind of the auxiliary apparatus mounted. The dual viewing optical unit 54 includes a beam splitter or composite prism 68 arranged on the optical axis of the eyepiece lens 16. A first ocular 70 is disposed in the optical path of one of light beams split by the beam splitter 68, while a second ocular 74 is disposed in the optical path of the other light beam which is split by the beam splitter 68 and transmitted through an additional image guide 72.

Where the code generator 66 is a resistor, the discriminating circuit 50 is so constructed that a DC power source 76 is connected with the connecting pins 46 and 48 through a resistor 84 and a series arrangement of resistors 78, 80 and 82 are connected in parallel with the DC power source 76, as shown in FIG. 3, for example. The inverted and non-inverted inputs of a first comparator 86 are connected with the connecting pin 48 and a connecting node between the resistors 78 and 80, respectively. Likewise, the inverted and non-inverted inputs of a second comparator 88 are connected with the connecting pin 48 and a connecting node between the resistors 80 and 82, respectively.

The aforementioned endoscope system is operated as follows. When neither of the auxiliary apparatuses 56 and 58 is attached to the eyepiece section 6 of the endoscope 2, the quantity of observation light supplied to the light guide 32 is adjusted by the luminance adjusting knob 37 so as to be suited to a simple observation state or first state in which observation is made through the eyepiece section 6 of the endoscope 2. Namely, when the rotary switch 52 is switched by the knob 37, the solenoid energizing circuit 40 is actuated to energize the solenoid 42. Thus, the stop 38 is moved to a first position where it intercepts a part of light path so that the light guide 32 may be supplied with observation light suited to the simple observation state. While the stop 38 is in the first position, the observation light suited to the simple observation state is projected on a region of interest 90 through the light guide 32. Reflected light from the region of interest 90 is supplied to the eyepiece 16 through the image guide 14, and an image of the region of interest 90 can be viewed with suitable brightness through the eyepiece 16.

When the camera unit 56 is attached to the eyepiece section 6 of the endoscope 2 while the control knob 37 is maintained in the aforesaid simple observation state, as shown in FIG. 1, the stop 38 is moved from the first position to a second position where proper observation light can be supplied to the light guide 32 in a camera unit mounting state or second state. Namely, when the camera unit 56 is attached to the eyepiece section 6, the connecting pins 18 and 20 in the eyepiece section 6 are connected with connecting pins (not shown) in the mounting section 60. If a code generator (not shown) in the camera unit 56 is a mere short-circuit wire, a short will be caused between the connecting pins 18 and 20. In the simple observation state, the circuit between the connecting pins 46 and 48 is opened and the comparators 86 and 88 of the discriminating circuit 50 shown in FIG. 3 generates low-level signals. In the camera unit mounting state, when a short is caused between the pins 46 and 48, the first comparator 86 produces a low-level signal, while the second comparator 88 produces a high-level signal. Receiving the high- and low-level signals from the discriminating circuit 50, the solenoid energizing circuit 40 de-energizes the solenoid 42 into the second state to move the stop 38 to the second position. As a result, observation light, the intensity of which is larger than that of the observation light for the simple observation state or first state, is supplied to the light guide 32 and projected on the region of interest 90. The intensity of reflected light from the region of interest 90 is larger than that of the reflected light obtained in the simple observation state. Since part of the reflected light is separated by a beam splitter (not shown) in the camera unit 56, the brightness of an image of the region of interest 90 observed through an eyepiece in the camera unit 56 may be maintained substantially equal to that of the image obtained in the simple observation state.

Where the dual viewing optical unit 54 is attached to the eyepiece section 6 of the endoscope 2, as shown in FIG. 2, the stop 38 is moved to a third position where it does not intercept the light from the lamp 34. Namely, when the mounting section 58 of the dual viewing optical unit 54 is attached to the eyepiece section 6 of the endoscope 2, the connecting pins 62 and 64 of the mounting section 58 are connected with the connecting pins 18 and 20 of the eyepiece section 6, respectively. If the code generator 66 of the dual viewing optical unit 54 is a resistor (not shown) with a certain resistance value, the resistor is connected between the connecting pins 46 and 48 by the connecting pins 18, 20, 62, 64, 22 and 24. Accordingly, high-level signals are produced from the first and second comparators 86 and 88 of the discriminating circuit 50 shown in FIG. 3 entirely to de-energize the solenoid 42, thereby moving the stop 38 to the third position. In consequence, observation light emitted from the light source lamp 34 is supplied to the light guide 32 without being intercepted by the stop 38. The observation light for such a dual viewing state or third state is larger in intensity than the observation lights for the camera unit mounting state or second state and the simple observation state or first state, and the intensity of reflected light from the region of interest 90 led into the image guide 14 is larger than those of the reflected lights observed in the first and second states. However, the reflected light is split into two substantially equal parts by the beam splitter 68, so that two images observed respectively through the first and second oculars 70 and 74 are substantially equal in brightness to each other and to the images observed in the first and second states.

Figure 4:
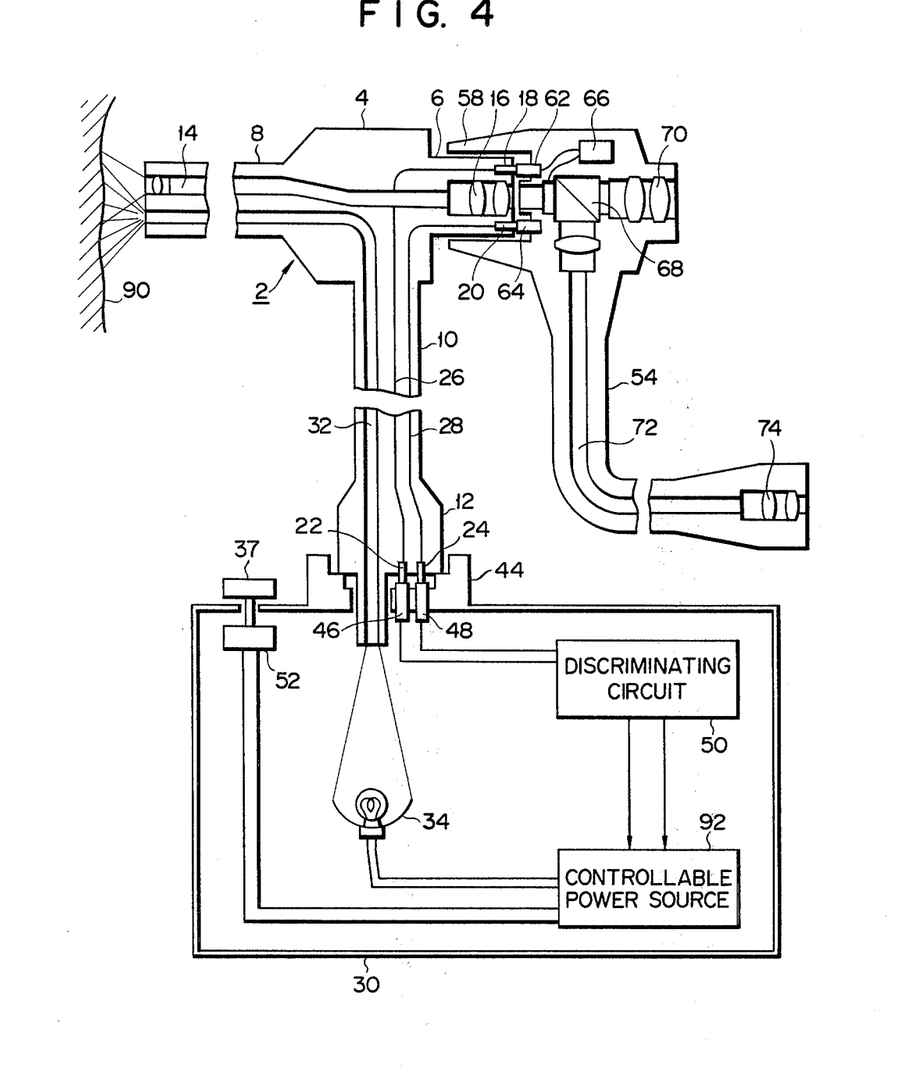
FIG. 4 is a schematic view for illustrating another embodiment of the endoscope system of the invention.

FIG. 4 shows an endoscope system according to another embodiment of this invention. In FIGS. 2 and 4, like reference numerals are used to designate like portions. In FIG. 4, a controllable power source 92 capable of changing electric power supplied to the lamp 34 is incorporated in the light source unit 30 as an electric power source for the lamp 34, and the stop 38, solenoid 42, and solenoid energizing circuit 40 are eliminated.

In the endoscope system shown in FIG. 4, when the knob 37 is set to establish the simple observation state or first state, the electric power supplied from the controllable power source 92 to the lamp 34 is reduced by the rotary switch 52, so that electric power for the first state is supplied to the lamp 34 and observation light for the first state is supplied to the light guide 32. Thus, an operator can observe an image of the region of interest 90 with proper brightness through the eyepiece section 6. Subsequently, when the camera unit 56 is attached to the endoscope 2, low- and high-level signals are supplied from the discriminating circuit 50 to the controllable power source 92, as already described in connection with the embodiment of FIG. 2. At this time, the controllable power source 92 is released from the first state set by the rotary switch 52 and switched to the second state. Namely, electric power for the second state is supplied from the controllable power source 92 to the lamp 34 so that the lamp 34 may emit observation light for the second state having a light intensity larger than that of the light for the first state. As a result, the image may be observed through the eyepiece of the camera unit 56 with the same brightness as in the first state, as mentioned before.

When the dual viewing optical circuit 54 is attached to the endoscope 2, moreover, high-level signals are delivered from the discriminating circuit 50, as mentioned before, and the controllable power source 92 supplies the lamp 34 with electric power for the third state to cause the lamp 34 to emit light of the highest luminous intensity among those of the lights for the first and second states. In the third state, therefore, the light guide 32 is supplied with observation light of the largest quantity, so that images can be observed with sufficient brightness through the two oculars 70 and 74 in the dual viewing optical unit 54, as mentioned before.

Figure 5:
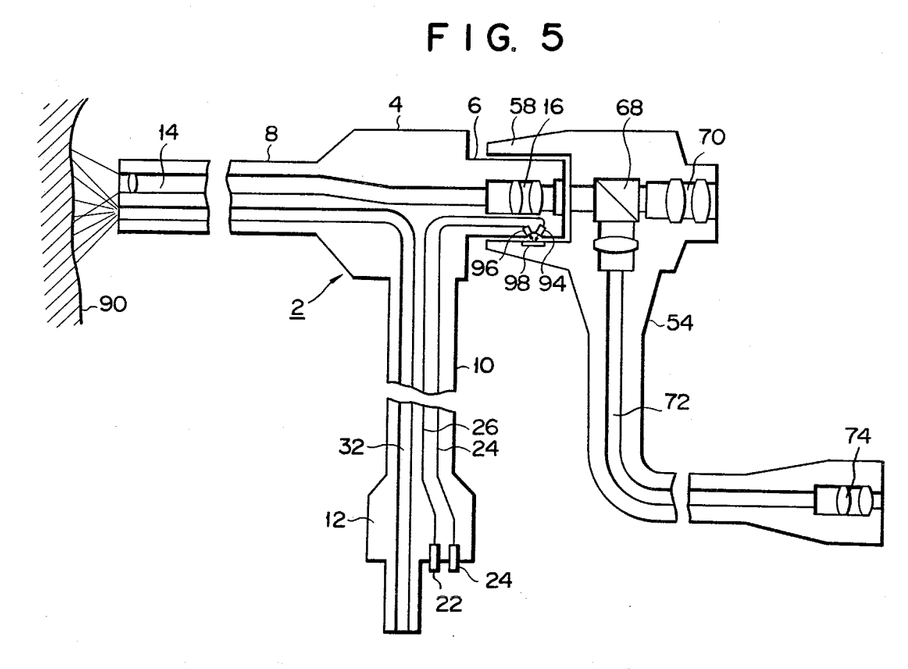
FIG. 5 is a schematic view for illustrating a modified embodiment of the endoscope system of the invention.
Figure 6:
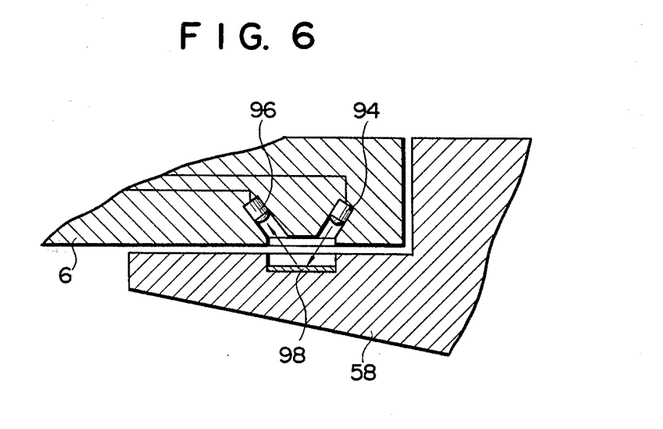
FIG. 6 is an enlarged sectional view showing part of FIG. 1.

Instead of using the code generator 66 for indicating the kind of the auxiliary apparatus 56 or 58 attached to the endoscope 2 and the connecting pins 18, 20, 62 and 62 shown in FIGS. 2 and 4, there may be used a combination of a light emitting element 94, a light sensing element 96, and a reflecting plate 98, as shown in FIGS. 5 and 6. In this case, as shown in FIG. 6, the light emitting element 94 and the light sensing element 96 are disposed in close vicinity to each other in the eyepiece section 6 of the endoscope 2 so that they may face the reflecting plate 98 disposed in the mounting section 58 or 60 of the auxiliary apparatus 54 or 56 when the eyepiece section 6 is attached to the mounting section 58 or 60. The reflection factor of the reflecting plate 98 depends on the kind of the auxiliary apparatus 54 or 56, so that the intensity of reflected light from the reflecting plate 98 incident upon the light sensing element 94 may vary with the kind of the auxiliary apparatus mounted. Thus, the discriminating circuit 50 is enabled to discriminate the kind of the mounted auxiliary apparatus when it is given a signal level converted by the light sensing element 94.

Figure 7:
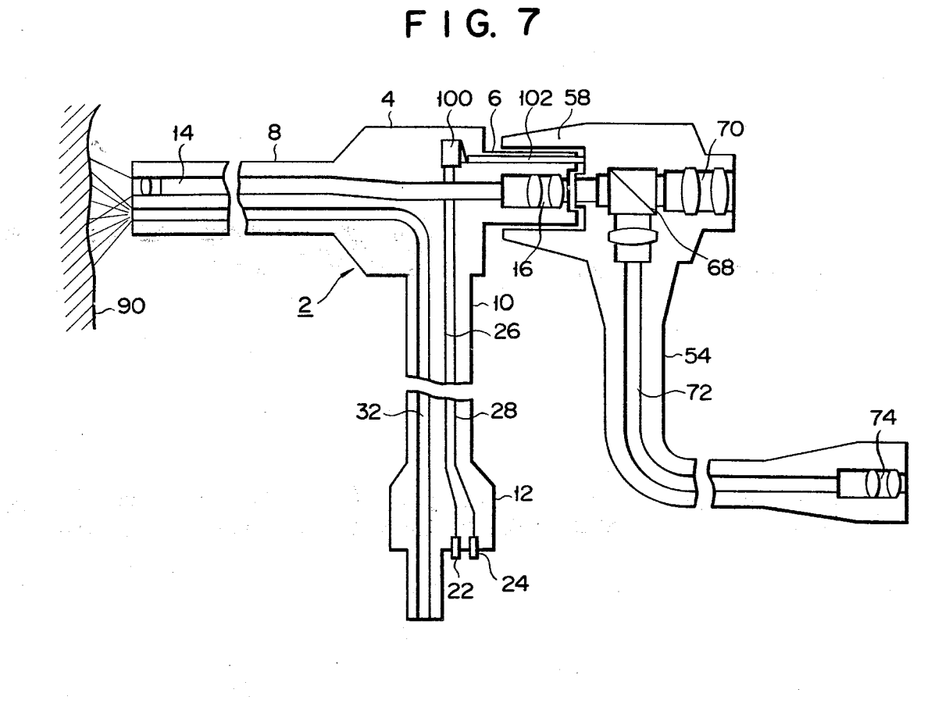
FIG. 7 is a schematic view for illustrating another modified embodiment of the endoscope system of the invention.

Moreover, the code generator 66 and the connecting pins 18, 20, 62 and 64 shown in FIGS. 2 and 4 may be replaced with a combination of a microswitch 100 and a push rod 102, as shown in FIG. 7. In this case, the microswitch 100 is disposed in the control section 4 of the endoscope 2, and a rod hole is bored in the control section 4 and the eyepiece section 6 so that the spring-biased push rod 102 is inserted in the rod hole with one end of the rod 102 being projected from the end face of the eyepiece section 6 and its other end being contacted with the contact of the microswitch 100.

In the embodiment shown in FIG. 7, when an auxiliary apparatus, e.g. the dual viewing optical unit 54, is attached to the eyepiece section 6, the push rod 102 is pushed against the spring-biasing force by the mounting section 58 to close the contact of the microswitch 100. As a result, it is detected that the auxiliary apparatus is attached to the eyepiece section 6. Further, the microswitch 100 may have two contacts one or both of which are to be closed in accordance with the displacement of the rod 102. In this case, a hole or recess is formed in each of the mounting sections 58 and 60 so that the push rod 102 may be pushed in accordance with the kind of the auxiliary apparatus. With such an arrnagement, the discriminating circuit 50 may give instructions for the second or third state to the solenoid energizing circuit 40 or the controllable power source 92 in accordance with the auxiliary apparatus attached to the eyepiece section 6.

According to this invention, as described above, there is provided an endoscope system in which the intensity of observation light supplied to the light guide of the endoscope is increased by only attaching an auxiliary apparatus to the eyepiece section of the endoscope, and is properly maintained in accordance with the kind of the auxiliary apparatus. Thus, the operation of the endoscope system is simplified, and the observation time may be reduced to ease a patient of his pain.

What is claimed is:

1. An endoscope system comprising:
   an endoscope including a light guide for transmitting an illumination light, an image guide for transmitting light reflected by a region of interest on which the illumination light from the light guide is projected, and a viewing section for viewing an image of the region of interest transmitted through the image guide;
   a light source for supplying illumination light to said light guide of said endoscope;
   an auxiliary apparatus capable of being removably attached to said viewing section of said endoscope; and
   detecting means for detecting the attachment of an auxiliary apparatus and the kind of said auxiliary apparatus attached to said viewing section of said endoscope and including means for setting the intensity of light fed into said light guide of said endoscope in accordance with the detected attachment of an auxiliary apparatus and as a function of the detected kind of said attached auxiliary apparatus.

2. An endoscope system according to claim 1, wherein said auxiliary apparatus comprises a camera unit.

3. An endoscope system according to claim 1, wherein said auxiliary apparatus auxiliary a dual viewing optical unit.

4. An endoscope system according to claim 1, wherein said detecting means includes limiting means for limiting the intensity of the light fed into said light guide; and means for releasing said limiting means from its light intensity limiting operation in accordance with said attachment and said detected kind of said auxiliary apparatus.

5. An endoscope system according to claim 1, wherein said detecting means includes means for regulating the electrical power supplied to said light source for regulating the intensity of the light emitted from said light source.

6. An endoscope system according to claim 1, wherein said detecting means includes:
   a stop located in the optical path of the illumination light emitted from said light source; and
   means for moving said stop to vary the intensity of illumination light fed into said light guide.

7. An endoscope system according to claim 1, wherein:
   said auxiliary apparatus includes a code generator therein; and said detecting means includes connecting pins disposed in said viewing section, said connecting pins being connected with said code generator in said auxiliary apparatus when said auxiliary apparatus is attached to said viewing section.

8. An endoscope system according to claim 7, wherein said code generator comprises a resistor having its resistance value being set according to the kind of said auxiliary apparatus.

9. An endoscope system according to claim 7, wherein said detecting means includes a microswitch disposed in said endoscope; and a movable push rod disposed in said viewing section and adapted to be pushed to close the contact of said microswitch when said auxiliary apparatus is attached to said viewing section.

10. An endoscope system according to claim 7, wherein said detecting means includes a light emitting element and a light sensing element disposed in said viewing section, and said auxiliary apparatus includes a reflector for directing light emitted from said light emitting element to said light sensing element when said auxiliary apparatus is attached to said viewing section.

11. An endoscope system according to claim 10, wherein said reflector has a reflection factor which is a function of the kind of said auxiliary apparatus.

* * * * *

UNITED STATES PATENT AND TRADEMARK OFFICE
CERTIFICATE OF CORRECTION

PATENT NO. : 4,407,272
DATED : October 4, 1983
INVENTOR(S) : Tatuya YAMAGUCHI

It is certified that error appears in the above-identified patent and that said Letters Patent is hereby corrected as shown below:

COLUMN 6 (claim 3), line 45, after "wherein said auxiliary apparatus" change the word "auxiliary" (second occurrence) to --comprises--.

Signed and Sealed this

Third Day of January 1984

[SEAL]

Attest:

GERALD J. MOSSINGHOFF

Attesting Officer  Commissioner of Patents and Trademarks